(12) United States Patent
Morozov

(10) Patent No.: US 9,033,977 B2
(45) Date of Patent: May 19, 2015

(54) ELECTROSURGICAL ELEMENT AND UTERINE MANIPULATOR FOR TOTAL LAPAROSCOPIC HYSTERECTOMY

(75) Inventor: Vadim Morozov, Towson, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 732 days.

(21) Appl. No.: 13/379,756

(22) PCT Filed: Jun. 9, 2010

(86) PCT No.: PCT/US2010/037866
§ 371 (c)(1),
(2), (4) Date: Dec. 21, 2011

(87) PCT Pub. No.: WO2010/151429
PCT Pub. Date: Dec. 29, 2010

(65) Prior Publication Data
US 2012/0109124 A1 May 3, 2012

Related U.S. Application Data

(60) Provisional application No. 61/220,246, filed on Jun. 25, 2009.

(51) Int. Cl.
*A61B 17/42* (2006.01)
*A61B 18/14* (2006.01)
*A61B 17/22* (2006.01)
(Continued)

(52) U.S. Cl.
CPC ......... *A61B 17/4241* (2013.01); *A61B 18/1477* (2013.01); *A61B 18/1492* (2013.01); *A61B 2017/22069* (2013.01); *A61B 2018/00214* (2013.01); *A61B 2018/00898* (2013.01); *A61B 2019/4027* (2013.01)

(58) Field of Classification Search
CPC ........... A61B 18/1405; A61B 18/1425; A61B 18/1475; A61B 18/1477; A61B 18/1485; A61B 18/1492; A61B 17/42; A61B 17/4241; A61B 2017/22069; A61B 2018/00214
See application file for complete search history.

(56) References Cited

U.S. PATENT DOCUMENTS 3,926,192 A 12/1975 Van Maren
4,000,743 A 1/1977 Weaver
(Continued)

OTHER PUBLICATIONS

CONMED Corporation Brochure for VCare: Vaginal-Cervical Ahluwalia Retractor-Elevator. Sep. 2007. 4 pages.

*Primary Examiner* — Christopher D Koharski
*Assistant Examiner* — Frances Oropeza
(74) *Attorney, Agent, or Firm* — Whiteford, Taylor & Preston LLP; Gregory M. Stone

(57) ABSTRACT

A vaginal cervical retractor used to maneuver and visualize the uterus during various medical examinations and procedures would include an inner tube provided with a movable assembly of plastic cups (cervical cup and vaginal cup) designed to be inserted into the uterine cavity and a retractable electrosurgical needle. A cervical cup is molded to a hollow outer shaft to form the movable cup assembly. This hollow shaft is provided through which the inner tube can be inserted. By utilizing a vaginal cervical retractor elevator provided with an inner rigid tubing, freely sliding vaginal cup and cervical cup designed to move on the inner tubing, attached to a hollow, plastic outer shaft into which the inner tubing can be inserted, and a retractable, flexible, electrosurgical needle, the colpotomy procedure can be performed with the improved uterine manipulator.

16 Claims, 3 Drawing Sheets

(51) Int. Cl.
 *A61B 18/00* (2006.01)
 *A61B 19/00* (2006.01)

(56) References Cited

U.S. PATENT DOCUMENTS

| | | | |
|---|---|---|---|
| 4,976,717 A | 12/1990 | Boyle | |
| 4,997,419 A | 3/1991 | Lakatos et al. | |
| 5,209,754 A | 5/1993 | Ahluwalia | |
| 5,437,665 A | 8/1995 | Munro | |
| 5,464,409 A | 11/1995 | Mohajer | |
| 5,520,698 A | 5/1996 | Koh | |
| 5,556,401 A | 9/1996 | Caillouette | |
| 5,643,285 A | 7/1997 | Rowden et al. | |
| 5,746,750 A | 5/1998 | Prestel et al. | |
| 5,759,183 A | 6/1998 | VanDusseldorp | |
| 5,840,077 A | 11/1998 | Rowden et al. | |
| 5,935,098 A | 8/1999 | Blaisdell et al. | |
| 6,048,351 A | 4/2000 | Gordon et al. | |
| 6,113,594 A | 9/2000 | Savage | |
| 6,132,428 A | 10/2000 | VanDusseldorp | |
| 6,174,317 B1 | 1/2001 | Engman | |
| 6,176,858 B1 | 1/2001 | Dequesne et al. | |
| 6,346,111 B1 | 2/2002 | Gordon et al. | |
| 6,423,075 B1 | 7/2002 | Singh et al. | |
| 6,572,631 B1 | 6/2003 | McCartney | |
| 6,780,180 B1 | 8/2004 | Goble et al. | |
| 6,893,435 B2 | 5/2005 | Goble | |
| 7,033,370 B2 | 4/2006 | Gordon et al. | |
| 7,060,077 B2 | 6/2006 | Gordon et al. | |
| 8,292,901 B2 * | 10/2012 | Auerbach et al. | 606/119 |
| 2001/0021854 A1 | 9/2001 | Donnez et al. | |
| 2006/0259035 A1 | 11/2006 | Nezhat et al. | |
| 2007/0179498 A1 | 8/2007 | MacDonald | |
| 2008/0009854 A1 | 1/2008 | Yates | |
| 2011/0190783 A1 | 8/2011 | Calderon | |

* cited by examiner

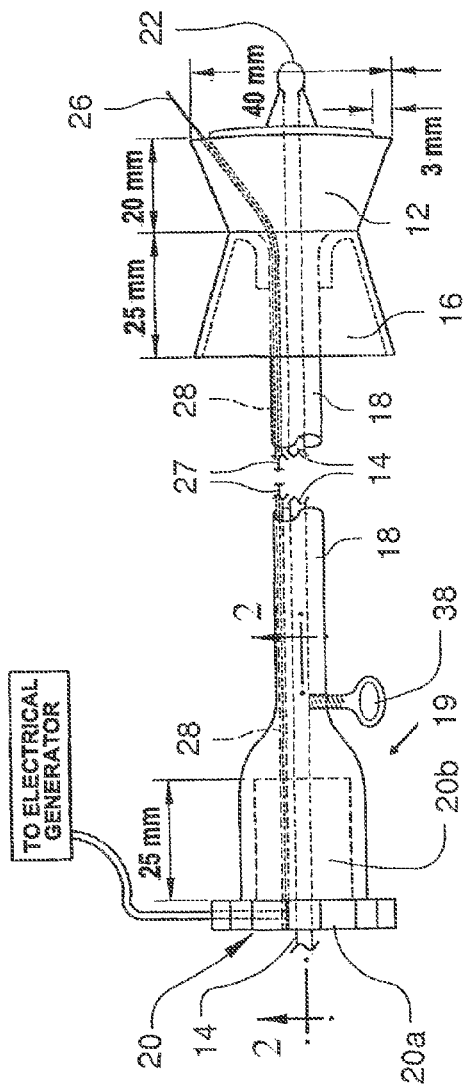
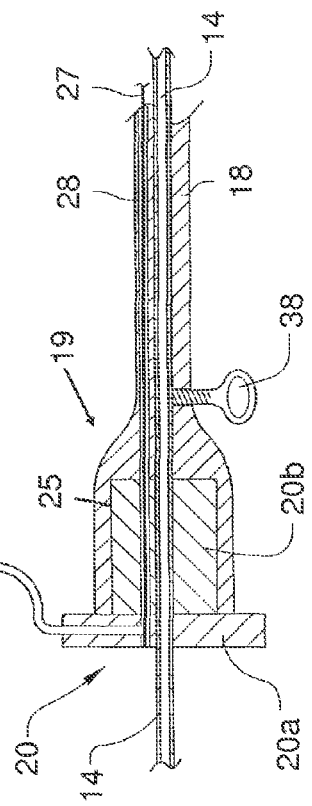
Figure 1
Figure 2

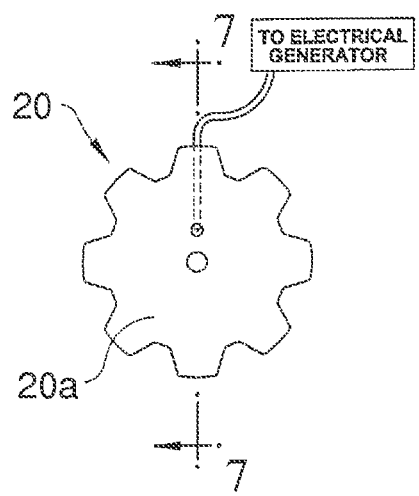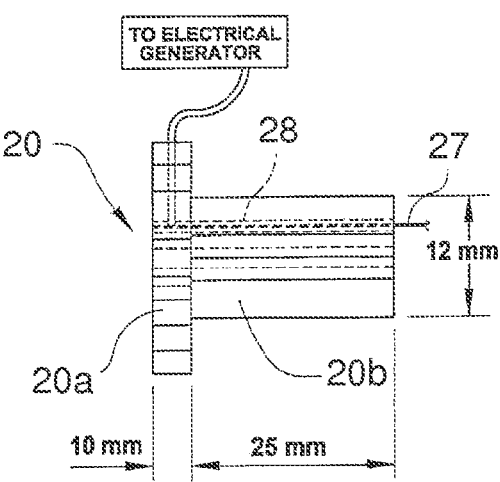
Figure 4  Figure 5
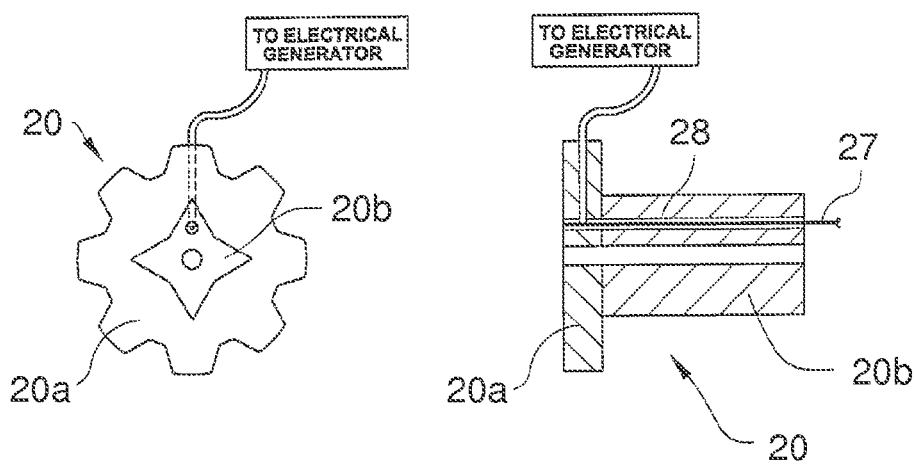
Figure 6  Figure 7

ELECTROSURGICAL ELEMENT AND UTERINE MANIPULATOR FOR TOTAL LAPAROSCOPIC HYSTERECTOMY

TECHNICAL FIELD

The present invention relates generally the field of surgical devices, and more particularly the invention relates to an improvement to a uterine manipulator device used for total laparoscopic hysterectomy procedures.

BACKGROUND ART

Various surgical procedures that are performed on women require that the women's uterus be manipulated such that the physician can view the uterus and cervix properly. Typical of these examinations and procedures would be a complete total laparoscopic hysterectomy, a partial laparoscopic hysterectomy, a colpotomy, as well as other procedures and examinations. Generally, during the performance of a laparoscopic procedure, a small incision is made in the wall of the abdomen and a laparoscope is inserted therethrough to permit visualization of the peritoneal cavity and the uterus.

According to multiple published reports, more than 600,000 hysterectomies are performed annually in the United States alone. Conventional hysterectomy surgical procedures typically involve one of four approaches—vaginal hysterectomy (VH), total abdominal hysterectomy (TAH), total laparoscopic hysterectomy (TLH), and laparoscopically assisted vaginal hysterectomy (LAVH). Vaginal, LAVH, and TLH have become more popular among surgeons because these approaches are less invasive than TAH, with VH being the least invasive approach. Close to 12% of those surgeries are done by a minimally invasive approach or laparoscopically, translating this into more than 70,000 surgeries annually in the United States, alone. VH is considered the least invasive; however, many women are not candidates for VH secondary to large uterus, previous surgery, and presence of adhesions. Unless medical indications require TAH (such as in the case of tumor removal and the associated need to avoid cell spillage), vaginal, TLH and LAVH are usually viewed as more preferable because each is less invasive when compared to major abdominal surgery. Thus, TLH and LAVH approaches usually result in shorter hospitalization and recovery times. With more advance instrumentation and better training of the gynecologic surgeons, the number of hysterectomies is expected to grow ever higher.

Difficulty, however, is encountered when employing TLH and LAVH techniques due to inherent limitations on visibility, anatomical identification, and the ability to manipulate organs (especially the uterus). In the case of TLH, these limitations are particularly pronounced because of higher degree of difficulty in securing the uterine arteries and cardinal ligaments associated with this approach. Altogether, TLH becomes a longer procedure, increasing intraoperative complications risks. During TLH, separation of the uterus and the cervix from the vagina remains one of the most difficult and cumbersome steps of the procedure. A higher degree of surgical difficulty has been found empirically to give rise to an increased risk of inadvertent damage to or dissection into the bladder, ureters, uterine vessels, and uterosacral and cardinal ligaments during the surgical procedure. Although the risk of inadvertent damage, for example, to the ureters can be minimized by the insertion of ureteral stints and/or peritoneal dissection to delineate ureter location, such techniques increase the complexity and the cost of the hysterectomy, and was not found to be effective.

A number of instruments have been developed to assist the physician in visualizing the uterus and facilitating the performance of these various examinations and procedures. Typical of these prior art instruments are those which are described in U.S. Pat. No. 3,926,192 to Van Maren; U.S. Pat. No. 4,000,743 to Weaver; U.S. Pat. No. 4,976,717 to Boyle; and U.S. Pat. No. 4,997,419 to Lakatos et al. The patent to Van Maren is directed to a medical instrument that is inserted into the vagina and passes through the cervix to enter the uterus. A cup-shaped member is provided whose end wall is connected to a source of vacuum, the cup-shaped member including a conical element designed to be placed against the cervical os. The patent to Weaver describes a uterine anteverter that includes an arcuately curved shield, which limits the distance a manipulating arm can be extended into the uterine cavity.

U.S. Pat. No. 5,209,754 to Ahluwalia describes a vaginal cervical retractor used to maneuver and visualize the uterus during various medical examinations and procedures. The Ahluwalia device has been commercialized by ConMed Corporation under the title Vcare for the Vaginal-Cervical Ahluwalia Retractor-Elevator.

Available instruments, however, do not address the issue of difficult and time-consuming separation of the uterus and the cervix from the vagina during total laparoscopic hysterectomy. Accordingly, there is a real and unsatisfied need in the surgical arts for a simplified total laparoscopic hysterectomy device that can reduce the time of the surgical procedure, minimize blood loss during surgery, minimize the risk of infection and injury to the patient during surgery, and minimize anesthesia time.

DISCLOSURE OF INVENTION

Accordingly, it is an object of the present invention to provide a surgical device that avoids the disadvantages of the prior art. Specifically, it is an object of the present invention to provide a combination uterine manipulator and electrosurgical element that avoids the disadvantages of the prior art.

It is an object of the present invention to provide an improvement to existing uterine manipulators. A related object of the present invention is to incorporate a retractable monopolar electrode needle into a uterine manipulator.

It is another object of the present invention to provide a surgical device that enables improved surgical control of the operating field. A related object of the present invention is to facilitate increased patient safety by minimizing surgical manipulation. A further related object is to reduce the cost of a total laparoscopic hysterectomy by eliminating the need for multiple surgical instruments and minimize anesthesia time.

These and other objects of the present invention are accomplished by enabling a device that can perform a total laparoscopic hysterectomy and colpotomy while maintaining pneumoperitoneum. The device of the present invention will allow a surgeon to manipulate the uterus while simultaneously performing colpotomy during total laparoscopic hysterectomy. By utilizing a vaginal cervical retractor elevator provided with an inner rigid tubing, inner and outer cups designed to move on the inner tubing, a hollow, plastic outer shaft into which the inner tubing can be inserted, and a retractable, flexible, electrosurgical needle, the colpotomy procedure can be performed with the improved uterine manipulator.

BRIEF DESCRIPTION OF THE DRAWINGS

The above and other features, aspects, and advantages of the present invention are considered in more detail, in relation to the following description of embodiments thereof shown in the accompanying drawings, in which:

FIG. 1 is a side elevational view of a combination uterine manipulator and electrosurgical element according to an embodiment of the present invention.

FIG. 2 is an enlarged cross-sectional view taken along lines 2-2 of FIG. 1.

FIG. 4 is a front elevational view of a locking and tightening collar of the surgical device according to an embodiment of the present invention.

FIG. 5 is a side elevational view of the locking and tightening collar of the surgical device according to an embodiment of the present invention.

FIG. 6 is a rear elevational view of a locking and tightening collar according to an embodiment of the present invention.

FIG. 7 is a cross-sectional view taken along lines 7-7 of FIG. 4.

BEST MODE(S) FOR CARRYING OUT THE INVENTION

Figure 3:
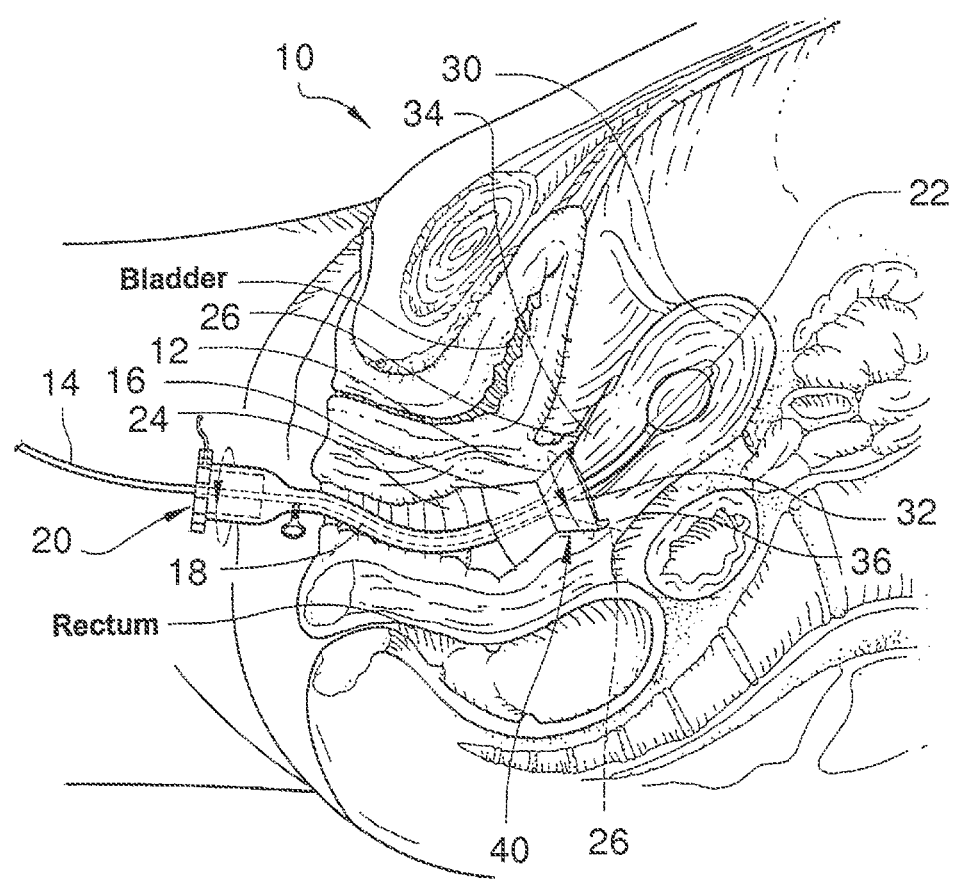
FIG. 3 is a partial section view of the surgical device, in use, according to an embodiment of the present invention.

The invention summarized above may be better understood by referring to the following description, which should be read in conjunction with the accompanying drawings. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

The present invention is an improvement of a pre-existing uterine manipulator. The improvement involves the addition of a retractable electrosurgical needle into the uterine manipulator.

Referring to the drawings, FIGS. 1 and 2 show the improved surgical instrument, indicated generally as 10, according to the present invention. The surgical instrument 10 includes a rigid manipulation shaft 14, which is used as a central assembly axis upon which the parts of the surgical instrument 10 are centered. A cervical cup 12 is molded to a manipulator tube 18 that surrounds the manipulation shaft 14. The cervical cup 12 and manipulator tube 18 act as one-piece for passage of a retractable electrosurgical needle 26 and monopolar electrode 27 through a tunnel 28. The manipulator tube 18 is slightly thickened and provides electrical insulation for the monopolar electrode 27. In a preferred embodiment, the tunnel 28 presents approximately 2 mm clearance. The manipulation shaft 14 typically comprises a metal alloy covered by a non-conductive sheath. The sheath is normally plastic. On the distal end of the manipulation shaft 14 is an inflatable balloon 22 to stabilize the manipulator tube 18 within the uterine cavity.

The manipulator tube 18 is sized and configured to conform to the sacral curve and is used for positioning the cervical cup 12 and the vaginal occlusion cup 16 during insertion of the surgical instrument 10. The cervical cup 12 is provided with a funnel-like base having a tapered body approximately 20 mm in length with a maximum diameter of approximately 40 mm. The cervical cup 12 displaces the cervix 32 away from the ureters, retracts the urinary bladder, and defines the colpotomy incision. Also mounted on the manipulator tube 18 is a vaginal occlusion cup 16, which includes a hole therein, allowing the uterine manipulator tube 18 to be inserted therethrough such that the vaginal occlusion cup 16 freely rotates and slides around the manipulator tube 18. The vaginal occlusion cup 16 has a tapered body approximately 25 mm in length with a maximum diameter of approximately 40 mm. The vaginal occlusion cup 16 prevents loss of pneumoperitoneum. When the surgical instrument 10 is inserted into the vagina 24, the cervical cup 12 surrounds and supports the cervix 32 and the vaginal occlusion cup 16 stretches the upper vaginal canal, allowing the manipulator tube 18 to perform its particular procedure.

Referring to FIG. 3, the surgical instrument 10 can be inserted into the vagina 24 so that the cervical cup 12 surrounds the cervix 32 and at least a portion of the uterus 30. The vaginal occlusion cup 16 make an airtight seal in the vagina 24 to maintain pneumoperitoneum when a circumferential colpotomy is completed. The balloon 22 is inserted inside the uterine cavity and is inflated to stay in place in the uterus 30 by injecting air into the balloon 22, as is know in the art. Once the manipulator tube 18 and cervical cup 12 are engaged, the assembly can be locked in place on the manipulation shaft 14 using thumbscrew 38, until such time that a colpotomy needs to be performed.

The flexible electrosurgical needle 26 and monopolar electrode 27 are housed inside the tunnel 28 that traverses the manipulator tube 18. The electrosurgical needle 26 remains in the tunnel 28 until the surgeon is ready to use it. The proximal end of the monopolar electrode 27 is attached to a standard operating room electrosurgical generator by means of a standard monopolar cord. The attachment point of the monopolar cord to the electrode 27 is located at the proximal end of a locking collar 20, as shown in FIG. 4. The locking collar 20 is used to advance and fix in place the electrosurgical needle 26. The locking collar 20 freely slides and rotates on the manipulation shaft 14, together with the manipulation tube 18 and cervical cup 12.

FIGS. 4-7 show the locking and tightening collar for the surgical instrument 10. The locking collar 20 includes a cogwheel front outer portion 20a, which is shaped for easy handling and rotation by the hand of a surgeon, and a rear star-shaped outer portion 20b. The diameter of the proximal end 19 of the manipulator tube 18 is slightly enlarged and hollowed to enable the star-shaped portion 20b to be engaged therein. The electrosurgical needle 26 is retracted and housed inside the manipulator tube 18 and cervical cup 12 by means of pulling on the locking collar 20 until ready to be engaged.

After completing all other necessary steps of the surgical procedure, the surgeon must be ready to perform a colpotomy, the separation of the uterus 30 and cervix 32 from the vagina 24. With the surgical instrument 10 in place, the electrosurgical needle 26 is advanced through the vaginal-cervical junction 36 into the pelvic cavity 34, under direct laparoscopic vision, by means of advancing the locking collar 20. The star-shaped portion 20b of the locking collar 20 is engaged into a correspondingly shaped receiving well 25 on the proximal end 19 of the manipulator tube 18. In a preferred embodiment, the receiving well 25 is approximately 25 mm deep and is sized and configured to receive the similarly sized star-shaped portion 20b of the locking collar 20. The star-shaped portion 20b fixes the assembly of the collar 20 within the manipulator tube 18 and provides rotational torque to the manipulator tube 18, cervical cup 12, and electrosurgical needle 26. The sharp point of the electrosurgical needle 26 punctures the tissue at the vaginal-cervical junction 36. The advancement of the electrosurgical needle 26 will be achieved by the cephalad sliding motion of the electrosurgical needle 26 and monopolar electrode 27 within the protective tunnel 28.

The monopolar electrode 27 is activated so that the electrosurgical needle 26 can then be rotated around the rigid manipulation shaft 14 as indicated by arrow 40. With the star-shaped portion 20b locked in place, rotating the cogwheel 20a results in electrosurgical separation of the uterus 30 and cervix 32 from the vagina 24. By utilizing the principles of electrosurgery applied to the monopolar electrosurgical needle 26, the separation of the uterus 30 and cervix 32 from the vagina 24 is performed by electric current passing through the monopolar electrode 27 and electrosurgical needle 26 while the surgical instrument is rotated in a circular pattern around the vaginal-cervical junction 36.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

INDUSTRIAL APPLICABILITY

The present invention is applicable to surgical instruments. The invention discloses a colpotomy assembly having an electrosurgical needle retractably mounted therein. The device can be made in industry and can be used in the medical field.

What is claimed is:

1. A colpotomy assembly adapted for insertion into a vaginal cavity for use in female pelvic surgical procedures comprising:
    a rigid elongated inner tube having a distal end and a proximal end;
    an elongated outer tube having a distal end and a proximal end surrounding said inner tube, said elongated outer tube being free to slide and rotate on said inner tube;
    an outer cervical cup having a top portion of a first diameter and a bottom portion having a second diameter less than said first diameter, said bottom portion of said outer cup provided with a hole therein, said outer cup being joined to the distal end of said elongated outer tube;
    an inner occlusion cup having a top portion of a third diameter and a bottom portion having a fourth diameter less than said third diameter, said bottom portion of said inner cup provided with a hole therein, said inner cup being free to slide and rotate on said elongated outer tube; and
    an electrosurgical needle retractably mounted in said outer cervical cup;
    wherein when said device is utilized, said inner cup would surround and support the cervix and said outer cup would stretch the upper vaginal canal, and wherein said electro surgical needle would puncture the vaginal-cervical junction to separate the uterus and cervix from the vagina.

2. The colpotomy assembly according to claim 1, said outer tube further including a tunnel having a monopolar electrode portion of said electrosurgical needle therein.

3. The colpotomy assembly according to claim 2, wherein said tunnel is electrically insulated.

4. The colpotomy assembly according to claim 1, said inner tube comprising a metal alloy and wherein said inner tube includes a non-conductive sheath to electrically insulate said inner tube.

5. The colpotomy assembly according to claim 1, wherein the distal end of said inner tube is provided with a balloon.

6. The colpotomy assembly according to claim 1 further comprising a locking collar surrounding said inner tube and removably attached to said outer tube, said locking collar being free to slide and rotate on said elongated inner tube.

7. The colpotomy assembly according to claim 6, said locking collar comprising a front outer portion and a rear outer portion,
    said front outer portion being configured for handling and rotation, and
    said rear outer portion being configured for engagement with the proximal end of said outer tube.

8. The colpotomy assembly according to claim 7, wherein the proximal end of said outer tube is configured for engagement with the rear portion of said locking collar.

9. A colpotomy assembly adapted for insertion into a vaginal cavity for use in female pelvic surgical procedures employing the inflation of an abdominal cavity with a gas to facilitate the accessibility to and visibility of female pelvic organs, said assembly comprising:
    an elongated shaft member presenting a proximal end and a distal end, said distal end of said shaft configured to be inserted into the vagina;
    an elongated outer tube having a distal end and a proximal end surrounding said elongated shaft member, said elongated outer tube being free to slide and rotate on said elongated shaft member;
    a handle mounted to said proximal end of said elongated outer tube;
    an outer cervical cup joined to the distal end of said elongated outer tube;
    an inner occlusion cup having a hole therein, said inner cup being free to slide and rotate on said elongated outer tube; and
    an electrosurgical needle retractably mounted in said outer cervical cup.

10. The colpotomy assembly according to claim 9, further comprising a balloon mounted to said distal end of said shaft, configured to engage a uterus.

11. The colpotomy assembly according to claim 9, said outer tube further including a tunnel having a monopolar electrode portion of said electrosurgical needle therein.

12. The colpotomy assembly according to claim 11, wherein said tunnel is electrically insulated.

13. The colpotomy assembly according to claim 9, said elongated shaft member comprising a metal alloy having a non-conductive sheath to electrically insulate said elongated shaft member.

14. The colpotomy assembly according to claim 9, said handle further comprising a locking collar surrounding said elongated shaft member and removably attached to said outer tube, said locking collar being free to slide and rotate on said elongated shaft member.

15. The colpotomy assembly according to claim 14, said locking collar comprising a front outer portion and a rear outer portion,
   said front outer portion being configured for handling and rotation, and
   said rear outer portion being configured for engagement with the proximal end of said outer tube.

16. The colpotomy assembly according to claim 14, wherein the proximal end of said outer tube is configured for engagement with the rear portion of said locking collar.

* * * * *